United States Patent [19]
Roberts

[11] 4,386,002
[45] May 31, 1983

[54] IMINES OF AMINODIPHENYL ESTHERS AS ANTIOXIDANTS AND LUBRICATING OILS AND GREASES CONTAINING SAME

[75] Inventor: John T. Roberts, Arlington Heights, Ill.

[73] Assignee: UOP Inc., Des Plaines, Ill.

[21] Appl. No.: 263,378

[22] Filed: May 12, 1981

[51] Int. Cl.³ .............................................. C10M 1/38
[52] U.S. Cl. .............................. 252/47.5; 252/51.5 R; 252/402; 252/403
[58] Field of Search ................. 252/47.5, 51.5 R, 402, 252/403

[56] References Cited

U.S. PATENT DOCUMENTS

| | | | |
|---|---|---|---|
| 2,216,752 | 10/1940 | Rosen | 252/47.5 X |
| 2,910,437 | 10/1959 | Symon | 252/51.5 R X |
| 2,910,437 | 10/1959 | Symon | 252/32 |
| 2,964,479 | 12/1960 | Cyba | 252/51.5 R X |
| 2,982,729 | 5/1961 | Cyba et al. | 252/40.7 |
| 3,122,575 | 2/1964 | Peterson et al. | 252/51.5 R X |
| 3,240,706 | 3/1966 | Cyba et al. | 252/51.5 R |
| 3,502,581 | 3/1970 | Cyba | 252/51.5 R |
| 4,309,294 | 1/1982 | Roberts | 252/47.5 X |

Primary Examiner—Andrew Metz
Attorney, Agent, or Firm—James R. Hoatson, Jr.; Eugene I. Snyder; William H. Page, II

[57] ABSTRACT

N-Arylmethylideneaminodiphenyl ethers are effective antioxidants for high pressure applications. The corresponding 4'-methoxy analogs, such as 4-benzylideneamino-4'-methoxydiphenyl ether and 2- and 4-pyridylmethylideneamino-4'-methoxydiphenyl ether, have particularly desirable properties.

19 Claims, No Drawings

IMINES OF AMINODIPHENYL ESTHERS AS ANTIOXIDANTS AND LUBRICATING OILS AND GREASES CONTAINING SAME

BACKGROUND OF THE INVENTION

A persistent problem common to virtually all petroleum products and petroleum-related products is their tendency to undergo oxidative degradation. Oxidation may occur even under the relatively mild conditions attending storage and transport, and is appreciably accelerated when operating conditions are conducive to oxidation processes, for example, the elevated temperatures experienced by lubricating oil. Such oxidative processes not only cause chemical degradation of the petroleum or petroleum-related product, but may also cause appreciable changes in desirable physical properties, such as viscosity, which lead to a deterioration of product performance characteristics. Additionally, the oxidative products themselves may attack materials in contact with the petroleum and petroleum-related products, such as metals in contact with transmission or lubricating oils, thereby causing inefficient performance and, in extreme cases, even mechanical failure.

The class of N,N'-dialkyl-4,4'-diaminodiphenyl ethers is known to have substantial antioxidant properties, and has found utility as an additive protecting petroleum and petroleum-related products against oxidation in their working environment as shown in U.S. Pat. No. 2,982,729. Unsubstituted 2,4'-diaminodiphenyl ether acts as an effective stabilizer against oxidative deterioration, U.S. Pat. No. 2,910,437, and mixtures of alkylated 4,4'- and 2,4'-diaminodiphenyl ethers act synergistically as an inhibitor according to U.S. Pat. No. 2,964,479. It now has been found that certain imines of aminodiphenyl ethers are effective oxidants in the aforementioned products. In some cases these ethers display antioxidant properties exceeding those of the symmetrical diaminodiphenyl ethers, thereby permitting their effective use at relatively lower levels. The antioxidants described herein possess the further advantage that structural changes within broad, but nonetheless well-defined, limits are possible, thereby permitting optimization of the antioxidant for a particular product in a specified use.

SUMMARY OF THE INVENTION

The principal object of this invention is to provide a method of inhibiting oxidation in petroleum products and petroleum-related products by the addition thereto of effective amounts of additives having antioxidant properties, and compositions thereof. An embodiment of this invention comprises the use of imines of aminodiphenyl ethers as an additive in said products. In a more specific embodiment the additives are arylmethylideneaminodiphenyl ethers and substituted derivatives thereof. In a still more specific embodiment the additives are 2- and 4-arylmethylideneaminodiphenyl ethers. In still another embodiment the additives are 4-arylmethylideneamino-4'-methoxydiphenyl ethers. In yet another embodiment the additives are present at a concentration from about 0.05 to about 5% by weight.

DESCRIPTION OF THE INVENTION

The materials of this invention are imines of aminophenyl ethers. More precisely, the materials may be designated as arylmethyleneaminodiphenyl ethers, where the aryl group is a benzene or substituted benzene nucleus, a fused ring aromatic nucleus, or a heteroaromatic nucleus. The term heteroaromatic means aromatic heterocyclic. The discovery of this invention is that the materials of such structure possess potent antioxidant properties and can be effectively used as an additive to retard and inhibit oxidation in petroleum products and petroleum-related products at concentrations as low as about 0.05% by weight.

The additives of the instant application have a common structure represented by the formula,

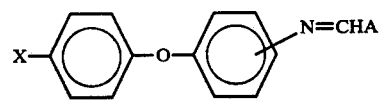

Although the arylmethyleneamino group, ACH=N—, may be at any position of the benzene ring, it is preferred that it be at the 2- or 4-position. Hence, the materials of this invention are 2- or 4-arylmethylideneaminodiphenyl ethers. The group represented by A in the above structure is an aromatic or heteroaromatic ring. Examples of such rings include benzene, naphthalene, anthracene, chrysene, pyridine, thiophene, pyrrole, furan, imidazole, oxazole, thiazole, quinoline, carbazole, pyrimidine, purine, and so forth. Where A is the benzene ring, it will be recognized that the resulting materials are N-benzylideneaminodiphenyl ethers. In other cases, it will be recognized that the resulting materials are aromatic and heteroaromatic analogs of the benzylideneaminodiphenyl ethers.

In some cases it is advantageous to have the aromatic or heteroaromatic ring bearing at least one substituent. Among those substituents often leading to enhanced desirable properties are halogen, especially chlorine, nitro, cyano, carboxyl, and hydroxyl moieties. Another class of substituents which may be effectively used in the materials described herein comprises alkyl, alkoxy, and alkylmercapto where the carbonaceous portion contains up to about 18 carbon atoms. Examples of the latter include methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, and octadecyl. The carbonaceous portion is saturated and may be either a straight or branched chain, although a branched chain is preferred because of increased solubility in products where their use is intended.

The moiety represented by X in the above structure may be hydrogen, but often will be an electronegative group such as a halogen, especially chlorine, hydroxy, or an alkoxy or alkylmercapto moiety where the carbonaceous portion contains up to about 18 carbon atoms. The carbonaceous portion is saturated and may be either a straight or branched chain, with preference going to a branched chain because of increased solubility in intended products. Examples of such moieties have been given above. In this branch of the invention alkoxy is a preferred moiety, and methoxy is particularly preferred.

Examples of suitable oxidants according to the foregoing description, cited solely for illustrative purposes, include the following named imines of 4-aminodiphenyl ether. It is to be understood that similarly substituted imines of 2- and 3-aminodiphenyl ether are equivalent examples and could be equally well cited here. 4-Benzylideneaminodiphenyl ether; 4-naphthylmethylideneamino-diphenyl ether; 4-anthracenylmethylideneaminodiphenyl ether; 4-pyridinylmethylideneaminodiphenyl ether; 4-thienylmethylideneamino-diphenyl ether; 4-furanylmethylideneaminodiphenyl ether, and similar diimines where the aromatic group is imidazole, oxazole, thiazole, quinoline, carbazole, pyrimidine, and the like; 4-methylbenzylideneaminodiphenyl ether; 4-t-butylbenzylideneaminodiphenyl ether; 4-methoxybenzylideneaminodiphenyl ether; 4-sec-pentoxybenzylideneamino-diphenyl ether; 4-chlorobenzylideneaminodiphenyl ether; 4-fluoro-benzylideneaminodiphenyl ether; 4-nitrobenzylideneaminodiphenyl ether; 4-methylmercaptobenzylideneamino diphenyl ether, and so forth; 4-benzylideneamino-4'-methoxydiphenyl ether; 4-benzylideneamino-4'-ethoxydiphenyl ether; 4-benzylideneamino-4'-octyloxydiphenyl ether; 4-benzylideneamino-4-chlorodiphenyl ether; 4-dibenzylideneamino-4'-fluorodiphenyl ether; 4-benzylideneamino-4'-bromodiphenyl ether; 4-benzylideneamino-4'-hexadecyloxydiphenyl ether, and so on.

The preparation of these materials is not novel and suitable methods will be recognized by those skilled in the art. One preparative route is the condensation of the 4-aminodiphenyl ether with an aromatic or heteroaromatic aldehyde, or mixtures of such aldehydes, to afford the Schiff base, or imine. Typically, such reaction is conducted in an inert solvent, such as an aliphatic or aromatic hydrocarbon or ethers, especially ethers of glycols and polyglycols, in the presence of an acid as catalyst, frequently p-toluenesulfonic acid or a similar acid, or Lewis acids, such as boron trifluoride, with subsequent recovery of the diimine as product. Reaction times of 8 to 16 hours at temperatures from about 90° to about 145° C. generally suffice.

The materials described herein may be used as antioxidants in a wide variety of petroleum and petroleum-related products, and other materials. For example, the materials may be used in lubricating oils and greases, either of synthetic or petroleum origin. Examples, cited for illustrative purposes only, include aliphatic esters, polyalkylene oxides, silicones, phosphoric and silicic acids, fluorine-substituted hydrocarbons, and the like. Lubricating oils of petroleum origin include motor lubricating oil, railroad type lubricating oil, marine oil, transformer oil, transmission oil, turbine oil, gear oil, differential oil, diesel lubricating oil, hydraulic oil, cutting oil, rolling oil, etc. Greases include petroleum grease, whale grease, wool grease, grease from inedible and edible fats, synthetic greases, such as those from mineral or synthetic oils containing hydrocarbon-soluble metal salts of fatty acids, and so forth. The materials of this invention also are suitable for the stabilization of plastics and rubbers obtained from polymerization of various petroleum-derived materials, such as polyethylene, polypropylene, polybutadiene, polystyrene, copolymers of ethylene and butadiene, and the like, polyacrylonitrile, polyacrylates, and so forth.

The materials may be effective as an antioxidant at levels as low as about 0.05% by weight. Higher concentrations, up to about 5% by weight, may be used if desired, although it will be recognized that it is economically advantageous to use these materials at as low a concentration as will be effective.

The materials described in the example are merely illustrative of this invention. It is to be understood that this invention is not to be limited thereto.

EXAMPLE 1

This example is illustrative of the general preparative method used. A mixture of 4-amino-4'-methoxydiphenyl ether (5.0 g, 23.3 mmol) and p-chlorobenzaldehyde (3.5 g, 25.0 mmol) in toluene (60 ml) was heated at reflux for 15 hours to remove the theoretical amount of $H_2O$. As the clear, yellow solution cooled to room temperature, a silver-grey solid crystallized. After cooling to 0° C. for 0.5 h, the mixture was suction filtered and air dried to recover a silver grey solid (7.3 g, 21.6 mmol, mp 154°-6°, 93% yield). Spectral data (nmr and ir) support the assigned structure of the corresponding imine.

EXAMPLES 2-10

A standardized test was used to screen the suitability of particular compounds as a stable antioxidant. Air at a constant rate of 50 ml per minute was bubbled through the test oil (a bright stock, Sentry 150 from Citgo) which is held at 275° F. in a thermostatically heated aluminum block. The test oil, to which was added the potential antioxidant, was contained in a large test tube with metal coupons of aluminum, brass, copper, and steel. Heating time for the test was a minimum of five days, but was continued until the oil spot test indicated that the test sample had significantly decomposed. Upon termination of the test the acid number (AN), change in the viscosity expressed as a percentage change ($\Delta V$ %), weight gain and weight loss of the coupons were determined. It has been found that the latter data are most significant for copper coupons, thus only these are reported herein.

The oil spot test consists of placing a drop of oil on a chromatography sheet. The appearance of the brown spot with a distinct perimeter or a spot with material at the center or with a definite ring indicates significant decomposition of the base oil. This was used to determine the length of the test subject to a five-day minimum time.

The results of testing are summarized in the accompanying table.

| PERFORMANCES OF ADDITIVES AS ANTIOXIDANTS | | | | | |
|---|---|---|---|---|---|
| Example | Additive[a,b] | S.D.[c] | AN[d] | Wt.loss[e] Cu | $\Delta V$ %[f] |
| 2 | none | 120[g] | 5.56 | 9.3 | 29.3 |
| 3 | A=4-(2-pyridyl) X=OCH$_3$ | 144 | 0.69 | 2.8 | 7.5 |
| 4 | A=4-(2-thiophenyl) X=OCH$_3$ | 144 | 2.91 | 5.3 | 22.3 |
| 5 | A=4-phenyl X=OCH$_3$ | 148 | 2.14 | 2.9 | 13.6 |
| 6 | A=4-(4-chlorophenyl) X=OCH$_3$ | 148 | 2.74 | 3.7 | 18.5 |
| 7 | A=4-phenyl X=H | 144 | 5.02 | 9.1 | 27.4 |
| 8 | A=4-(1-naphthyl) X=OCH$_3$ | 172 | 4.19 | 1.1 | 27.3 |
| 9 | A=2-(2-pyridyl) X=OCH$_3$ | 144 | 0.98 | 2.8 | 8.1 |

-continued

PERFORMANCES OF ADDITIVES AS ANTIOXIDANTS

| Example | Additive[a,b] | S.D.[c] | AN[d] | Wt.loss[e] Cu | ΔV %[f] |
|---|---|---|---|---|---|
| 10 | Ethyl 702[h] | 172 | 2.83 | 3.8 | 17.3 |

[a]All additives at 0.5 weight % unless otherwise indicated.
[b]Additives have the formula shown, vide supra, with A and X being designated in this column.
[c]Time, in hours, for onset of significant decomposition.
[d]Acid number, ASTM D-974
[e]Copper loss in mg.
[f]Percent change in kinematic viscosity at 100° F.
[g]Decomposition began prior to 120 hours, but test ran for 120 hours.
[h]A commercial product from Ethyl Corporation.

As the data show, the additives described in this invention lead to a substantial decrease in acid number and cause substantially less copper loss when compared to the blank. Equally important is the observation that the additives herein cause only a minor change in viscosity over the lifetime of the test.

What is claimed is:

1. A method of inhibiting oxidation in lubricating oils and greases comprising adding thereto an oxidation inhibiting amount of a material with the structure,

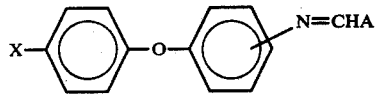

where A is selected from the group consisting of unsubstituted and ring-substituted aromatic and heteroaromatic rings, and X is selected from the group consisting of hydrogen, halogen, alkoxy and alkylmercapto wherein the carbonaceous portion contains up to about 18 carbon atoms.

2. The method of claim 1 wherein said lubricating oils and greases are synthetic or of petroleum origin.

3. The method of claim 1 where X is hydrogen or methoxy.

4. The method of claim 3 wherein A bears at least one other moiety selected from the group consisting of halogen, nitro, cyano, carboxyl, hydroxyl, alkyl, alkoxy, and alkylmercapto where the carbonaceous portion contains up to about 18 carbon atoms.

5. The method of claim 3 wherein A is selected from the group consisting of benzene, naphthalene, anthracene, pyridine, thiophene, pyrrole, furan, imidazole, oxazole, thiazole, quinoline, and carbazole rings.

6. The method of claim 5 wherein A is the benzene ring.

7. The method of claim 5 wherein A is the pyridine ring.

8. The method of claim 5 wherein A is the naphthalene ring.

9. The method of claim 5 wherein A is the thiophene ring.

10. The method of claim 1 wherein the oxidation inhibiting amount is from about 0.05% to about 5% by weight based on said lubricating oils and greases.

11. A composition comprising a major amount of a lubricating oil or grease and a minor amount from about 0.05% to about 5% by weight of a material with the structure,

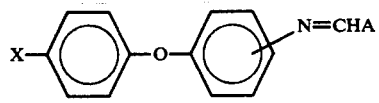

where A is selected from the group consisting of unsubstituted and ring-substituted aromatic and heteroaromatic rings, and X is selected from the group consisting of hydrogen, halogen, alkoxy and alkylmercapto wherein the carbonaceous portion contains up to about 18 carbon atoms.

12. The composition of claim 11 wherein said lubricating oils and greases are synthetic or of petroleum origin.

13. The composition of claim 11 where X is hydrogen or methoxy.

14. The composition of claim 13 wherein A bears at least one other moiety selected from the group consisting of halogen, alkyl, alkoxy, and alkylmercapto where the carbonaceous portion contains up to about 18 carbon atoms, nitro, cyano, carboxyl, and hydroxyl moieties.

15. The composition of claim 13 wherein A is selected from the group consisting of benzene, naphthalene, anthracene, pyridine, thiophene, pyrrole, furan, imidazole, oxazole, thiazole, quinoline, and carbazole rings.

16. The composition of claim 15 wherein A is the benzene ring.

17. The composition of claim 15 wherein A is the pyridine ring.

18. The composition of claim 15 wherein A is the naphthalene ring.

19. The composition of claim 15 wherein A is the thiophene ring.

* * * * *